US009668484B2

(12) United States Patent
Bristow

(10) Patent No.: US 9,668,484 B2
(45) Date of Patent: Jun. 6, 2017

(54) SYNERGISTIC HERBICIDAL COMPOSITION AND USE THEREOF

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/958,339

(22) Filed: Dec. 3, 2015

(65) Prior Publication Data

US 2016/0286813 A1    Oct. 6, 2016

(30) Foreign Application Priority Data

Mar. 30, 2015    (GB) .................................. 1505464.6

(51) Int. Cl.
*A01N 41/10*    (2006.01)
*A01N 47/36*    (2006.01)
*C07D 401/12*    (2006.01)

(52) U.S. Cl.
CPC ............. *A01N 47/36* (2013.01); *A01N 41/10* (2013.01); *C07D 401/12* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,550,238 A | * | 8/1996 | Chiang ................ | C07D 521/00 544/206 |
| 6,046,134 A | * | 4/2000 | De Gennaro .......... | A01N 41/10 504/133 |
| 2013/0252818 A1 | | 9/2013 | Lovejoy et al. | |
| 2015/0031877 A1 | * | 1/2015 | Hiratsuka .............. | A01N 43/84 544/105 |

FOREIGN PATENT DOCUMENTS

| | | | |
|---|---|---|---|
| CN | 101647457 | * | 2/2010 |
| CN | 101671328 A | | 3/2010 |
| CN | 101743988 A | | 6/2010 |
| CN | 101961023 A | | 2/2011 |
| CN | 102265883 A | | 12/2011 |
| EP | 341011 | * | 11/1989 |
| WO | 9748276 A | | 12/1997 |
| WO | WO 2006/021743 | * | 3/2006 |
| WO | 2013143927 A1 | | 10/2013 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
HCAPLUS abstract 1999:261209 (1999).*
Roberts, R.M. et al. Modern Experimental Organic Chemistry. Holt, Rinehart and Winston, New York, 1979, pp. 49-58.*
HCAPLUS abstract 2010:217690; abstracting CN 101647457 (Feb. 2010).*
Derwent abstract 2010-D96492; abstracting CN 101647457 (Feb. 2010).*
Calculating Synergistic and Antagonistic Responses of Herbicide Combinations; S. R. Colby, Weeds, vol. 15, No. 1 (Jan. 1967), pp. 20-22, Weed Science Society of America and Allen Press.
Herbicide Handbook, Weed Science Society of America, Seventh Edition—1994, p. 318.
International Search Report and Written Opinion, mailed Dec. 21, 2016 (PCT/CN2016098776).
International Search Report, mailed Jul. 4, 2016 (PCT/CN2016077620).
Written Opinion, mailed Jul. 4, 2016 (PCT/CN2016077620).
Tong, Jun et al., New Synthetic Method of Rimsulfuron, Chemical Intermediate, Dec. 31, 2009, No. 5, pp. 29-31.
Lu, Xinxin et al., Synthesis of Sulfonylurea Herbicide Rimsulfuron, Modren Agrochemicals, Jun. 30, 2007, No. 3, vol. 6, pp. 13-15 (p. 15, section 2.8).
Zhang, Dayong et al., Synthesis of Rimsulfuron, Chinese Journal of Pesticides, Dec. 31, 2005, No. 12, vol. 44, pp. 541-543 (p. 543, section 1.2.5).
Tan, Xiaojun et al., Synthesis of Sulfonylurea Herbicide Rimsulfuron, Fine Chemical Intermediates, Jun. 30, 2005, No. 3, vol. 35, pp. 26-27 (p. 27, section 2.5).
Bogdan, Ileana et al., Researches on the Effectiveness of Two Chemical Weed Control Strategies in Maize, Maize Bulletin UASVM, Agriculture, Dec. 31, 2010, No. 1, vol. 67, pp. 40-47 (p. 41, table 1, V8).
Feng, Xiangtong et al., Sythesis of Rimsulfuron, Agrochemicals Research & Application, Jun. 30, 2016, No. 3, vol. 10, pp. 17-19 (p. 19, right column, second paragraph).

* cited by examiner

*Primary Examiner* — John Pak
(74) *Attorney, Agent, or Firm* — Dickinson Wright PLLC

(57) ABSTRACT

A herbicidal composition is provided, the composition comprising: (A) the crystalline modification I of 2-(4-mesyl-2-nitrobenzoyl)cyclohexane-1,3-dione (mesotrione); and (B) the crystalline modification I of 1-(4,6-dimethoxypyrimidin-2-yl)-3-(3-ethylsulfonyl-2-pyridylsulfonyl)urea (rimsulfuron). A method of controlling plant growth at a locus comprises applying to the locus herbicidally effective amounts of both (A) the crystalline modification I of 2-(4-mesyl-2-nitrobenzoyl)cyclohexane-1,3-dione (mesotrione); and (B) the crystalline modification I of 1-(4,6-dimethoxypyrimidin-2-yl)-3-(3-ethylsulfonyl-2-pyridylsulfonyl)urea (rimsulfuron).

32 Claims, 3 Drawing Sheets

SYNERGISTIC HERBICIDAL COMPOSITION AND USE THEREOF

CROSS-REFERENCE TO RELATED APPLICATION

This U.S. Patent Application claims priority to Great Britain Patent Application No. GB 1505464.6, filed Mar. 30, 2015 entitled "A NOVEL FORM OF RIMSULFURON, A PROCESS FOR ITS PREPARATION AND USE OF THE SAME," the entire disclosure of the application being considered part of the disclosure of this application and hereby incorporated by reference.

BACKGROUND

1. Field

The present disclosure relates to a synergistic herbicidal composition containing mesotrione and rimsulfuron, each in particular crystal modifications. The composition finds use in controlling the growth of undesirable plant, particularly in crops, including using the aforementioned composition.

2. Description of Related Art

The protection of crops from undesirable plant, which inhibits crop growth, is a constantly recurring problem in agriculture. To solve this problem, researchers are trying to produce an extensive variety of chemicals and chemical formulations effective in the control of such undesirable growth. Chemical herbicides of many types have been disclosed in the literature and a large number are in commercial use.

Some herbicidal active ingredients have been shown to be more effective when applied in combination rather than applied individually, this effect being referred to as "synergism." According to *Herbicide Handbook* of the Weed Science Society of America, Seventh Edition, 1994, page 318, "synergism" is an interaction of two or more factors such that the effect when combined is greater than the predicted effect based on the response to each factor applied separately.

The compound 2-(4-mesyl-2-nitrobenzoyl)cyclohexane-1,3-dione has the common name "mesotrione". Mesotrione is a substance that can form polymorph crystals. Two different forms, crystalline modifications I and II, of mesotrione are described in WO2006021743, which is incorporated herein by reference for all purposes. Mesotrione is active as a herbicide and is now commercially available in a range of formulations for controlling the growth of undesirable plant.

The compound 1-(4,6-dimethoxypyrimidin-2-yl)-3-(3-ethylsulfonyl-2-pyridylsulfonyl)urea, having the common name "rimsulfuron", is a member of the sulfonylurea group of chemicals. Rimsulfuron is a potent herbicide having high selectivity, high efficiency, low toxicity and other desirable attributes. It is used post-emergence on crops, such as maize and potatoes, against a variety of annual and perennial grasses and broadleaved weeds. It is rather less toxic towards algae and is of generally low toxicity towards most other wildlife.

The commercially available rimsulfuron, which is usually manufactured by the process described in EP0341011 A1, which is incorporated herein by reference for all purposes, is present in an amorphous state.

It has been found that rimsulfuron in amorphous state is highly viscous, which is not suitable for being prepared as compositions or formulations having spray equipment cleanout property. Rimsulfuron residues stay in the spray equipment after spraying. Adequate cleanout may require a rinsing procedure that is not only time-consuming but also results in wastewater disposal problems. Therefore, there is a need to provide a novel form of rimsulfuron with increased solubility and decreased viscosity.

It has been found that a crystalline form of rimsulfuron, termed hereinafter "crystalline modification I", has an increased solubility, decreased viscosity and improved spray equipment clean-out properties (referred as "crystal form A" in UK patent application GB1505464.6, filed on 30 Mar. 2015, and incorporated herein by reference). The crystalline modification I of rimsulfuron of the invention exhibits at least 3 of the following reflexes as 2θ values in an X-ray powder diffractogram recorded using Cu-Kα radiation at 25° C.:

$2\theta=10.868\pm0.2$ (1)

$2\theta=12.248\pm0.2$ (2)

$2\theta=12.845\pm0.2$ (3)

$2\theta=14.249\pm0.2$ (4)

$2\theta=15.039\pm0.2$ (5)

$2\theta=16.120\pm0.2$ (6)

$2\theta=17.434\pm0.2$ (7)

$2\theta=18.010\pm0.2$ (8)

$2\theta=19.699\pm0.2$ (9)

$2\theta=21.801\pm0.2$ (10)

$2\theta=22.568\pm0.2$ (11)

$2\theta=26.567\pm0.2$ (12).

SUMMARY

It has been surprisingly found that combining the crystalline modification I of mesotrione with the crystalline modification I of rimsulfuron provides a composition having a synergistic activity, that is, an increased herbicidal activity, compared with the activity expected from the activity of the two components when applied individually.

Accordingly, in a first aspect, the invention provides a herbicidal composition comprising:

(A) the crystalline modification I of 2-(4-mesyl-2-nitrobenzoyl)cyclohexane-1,3-dione (mesotrione); and (B) the crystalline modification I of 1-(4,6-dimethoxypyrimidin-2-yl)-3-(3-ethylsulfonyl-2-pyridylsulfonyl)urea (rimsulfuron).

The composition of an embodiment of the invention is of particular use for controlling the growth of undesirable plant.

In a second aspect, the invention provides a method of controlling the growth of undesirable plant comprising applying to the plant or to the locus thereof a herbicidally effective amount of the herbicidal composition of the first aspect of the present invention.

In a further aspect, the invention provides the use of the herbicidal composition of the first aspect of the invention in control of undesirable plant growth at a locus.

DETAILED DESCRIPTION OF SPECIFIC EMBODIMENTS

Figure 1:
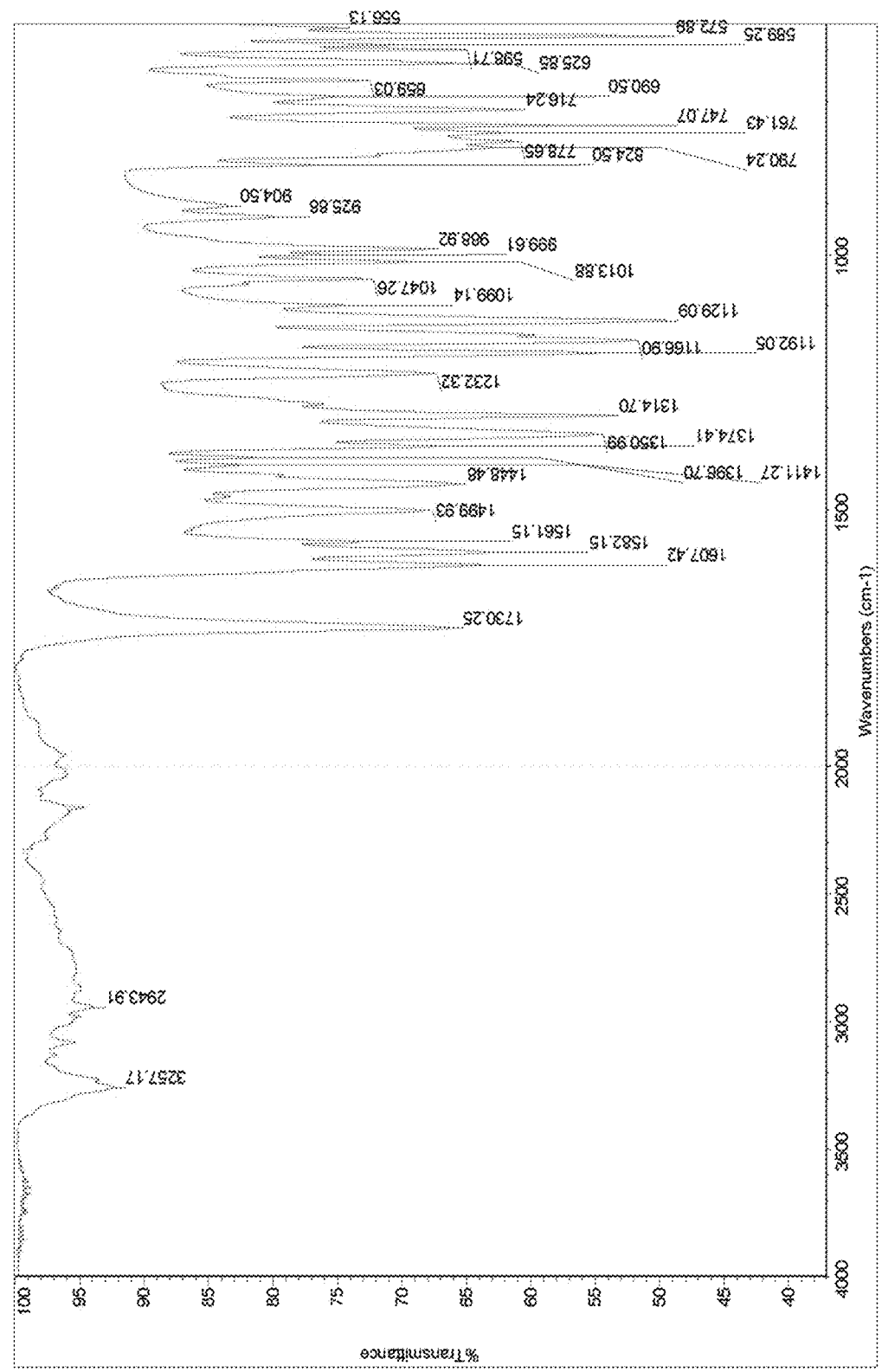
FIG. 1 is an infrared (IR) spectrograph of crystalline modification I of rimsulfuron, according to an embodiment of the invention.

The references to the crystalline modifications I and II of mesotrione as used herein, refer to the crystalline modification of mesotrione disclosed in WO2006021743, where they are described as Form I and Form II, respectively, which is incorporated herein by reference in its entirety for all purposes.

The XRD diffraction data for mesotrione crystal form I are given below.

| Peak Position (2-Theta) | Peak Position (d spacing) |
|---|---|
| 8.52 | 10.34 |
| 17.08 | 5.18 |
| 17.43 | 5.08 |
| 18.74 | 4.73 |
| 19.04 | 4.66 |
| 19.31 | 4.59 |
| 19.52 | 4.54 |
| 21.15 | 4.20 |
| 25.73 | 3.46 |
| 28.66 | 3.11 |

Alternatively, the crystalline modification I mesotrione may have a slightly shifted XRD spectrum:

| Peak Position (2-Theta) | Peak Position (d spacing) |
|---|---|
| 8.44 | 10.47 |
| 17.35 | 5.11 |
| 17.55 | 5.05 |
| 18.67 | 4.75 |
| 18.98 | 4.68 |
| 19.24 | 4.61 |
| 19.45 | 4.56 |
| 21.06 | 4.22 |
| 25.64 | 3.47 |
| 28.55 | 3.13 |

The term "herbicide" as used herein, refers to a compound that controls the growth of plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

The term "plants" refers to all physical parts of a plant, including shoots, leaves, needles, stalks, stems, fruit bodies, fruits, seeds, roots, tubers and rhizomes.

The term "locus" refers to the place on which the plants are growing, the place on which the plant propagation materials of the plants are sown or the place on which the plant propagation materials of the plants will be sown.

"At least one" designates a number of the respective compounds or components of 1, 2, 3, 4, 5, 6, 7, 8, 9 or more, preferably 1, 2, or 3.

The synergistic herbicidal composition, the method and use of the present invention are suitable for controlling undesirable plant growth in a range of crops, including: cereals, for example wheat, barley, rye, oats, corn, rice, sorghum, triticale and related crops; fruit, such as pome fruit, stone fruit and soft fruit, such as apples, pears, plums, peaches, pistachio, almonds, cherries, and berries, for example grape, banana, strawberries, bushberry, cranberries, raspberries, blackberries and blueberries; leguminous plants, for example beans, lentils, peas, and soybeans; oil plants, for example oilseed rape, mustard and sunflowers; cucurbitaceae, for example cantaloupe, marrows, cucumbers, melons, pumpkin, squash and watermelon; fibre plants, for example cotton, flax, hemp, and jute; citrus fruit, such as oranges, lemons, grapefruit and mandarins; and vegetables, for example spinach, lettuce, asparagus, cabbages, carrots, onions, tomatoes, potatoes, paprika, garlic and leeks; coffee; sugarcane; hops; tree nuts; as well as ornamentals, for example flowers, such as roses, shrubs, broad-leaved trees and evergreens, such as conifers. Preferably, the composition described herein is used to treat cereals, fruits, vegetables, fibre and leguminous plants. More preferably, the composition described herein is used to treat tomato, corn, potato, wheat, soybean and cotton.

The control of undesirable plant growth in such crops may be achieved by applying to the locus (A) the crystalline modification I of 2-(4-mesyl-2-nitrobenzoyl)cyclohexane-1, 3-dione (mesotrione), which is identified as Form I in WO 2006/021743 and (B) the crystalline modification I of 1-(4, 6-dimethoxypyrimidin-2-yl)-3-(3-ethylsulfonyl-2-pyridylsulfonyl)urea (rimsulfuron) in suitable amounts.

The active compounds (A) and (B) may be applied to the locus together or separately. If applied separately, active compounds (A) and (B) may be applied at the same time and/or consecutively. The control may comprise applying to the undesirable plant or the locus thereof a herbicidally effective amount of the herbicidal composition.

It has been surprisingly found that a combination of (A) the crystalline modification I of 2-(4-mesyl-2-nitrobenzoyl) cyclohexane-1,3-dione (mesotrione) and (B) the crystalline modification I of 1-(4,6-dimethoxypyrimidin-2-yl)-3-(3-ethylsulfonyl-2-pyridylsulfonyl)urea (rimsulfuron) exhibits a synergistic action in the control of many weeds, particularly, but not limit to, broadleaved weeds, grasses and sedges. For example, weeds treatable according to an embodiment of the invention include:

African Rue (*Peganum Harmala*), Alkali Mallow (*Malvella leprosa*), Alligatorweed (*Alternantha philoxeroides*), Alsike Clover (*Trifolium hybridum*), Amaranth, Amaranth (*Amaranthus* spp.), Palmer (*Amaranthus palmeri*), Amaranth, Powell (*Amaranthus powellii*), Amaranth, spiny (*Amaranthus spinosus*), Annual Broomweed (*Gutierrezia dracunculoides*), annual knawel (*Scleranthus annuus*), annual mercury (*Mercurialis annua*), Annual Pricklepoppy (*Argemone polyanthemos*), Annual Sowthistle (*Sonchus oleraceus*), Antelope Horn (*Asclepias viridis*), Asiatic Hawksbeard (*Youngia japonica*), Atriplex (*Chenopodium orach*), Balsam Gourd (*Ibervillea lindheimeri*), Balsam-Apple (*Momordica charantia*), Barnyardgrass (*Echinochloa crusgalli*), Bastard Toadflax (*Comandra umbellata*), Beggarweed (*Desmodium* spp.), Bindweed, Field (*Convolvulus arvensis*), Bindweed, Hedge (*Convolvulus sepium*), Bindweed, Texas (*Convolvulus equitans*), Birdsfoot Trefoil (*Lotus corniculatus*), Bittercress, Smallflowered (*Cardamine parviflora*), Bitterweed (*Hymenoxys odorata*), Bitterweed, Brown (*Helenium badium*), Black Medic (*Medicago lupulina*), black mustard, Black Nightshade (*Solanum americanum*), black nightshade (*Solanum* spp), Blackfoot Daisy (*Melampodium leucanthum*), Blackseed Plantain (*Plantago rugelii*), Bladderpod (*Lesquerella gracilis*), blue/purple mustard, Bluegrass, annual (*Poa annua*), Bracted Plantain (*Plantago aristata*), broadleaf dock, Broadleaf Plantains (*Plantago* spp.), Broadleaf signalgrass (*Urochloa platyphylla*), Buckhorn Plantain (*Plantago lanceolata*), Buffalo Gourd (*Cucurbita foetidissima*), Buffalobur (*Solanum rostratum*), Bulbous Buttercup (*Ranunculus bulbosus*), Bull Thistle (*Cirsium vulgare*), bur buttercup, Bur Clover (*Medicago hispida*), Burcucumber (*Sicyos angulatus*), Bushy Buttonweed (*Spermacoce assurgens*), bushy wallflower, Bushy Wallflower (*Erysimum repandum*), Butterweed (*Senecio glabellus*), Camphorweed (*Heterotheca subaxillaris*), Canada Rush (*Juncus Canadensis*), Canada Thistle (*Cirsium arvense*), Carolina False Dandelion (*Pyrrhopappus carolinianus*), Carolina *geranium*, Carpetweed (*Mollugo verticillata*), Catchweed Bedstraw (*Galium aparine*), Centella, Chamberbitter (*Phyllanthus urinaria*), Chamomile, false (*Tripleurospermum perforatum*), Chicory (*Cichorium intybus*), Cinquefoil, cinquefoil (*Potentilla* spp.), Clammy Groundcherry (*Physalis heterophylla*), clasping pepperwee, Climbing Hempweed (*Mikania scandens*), Coast fiddleneck, Coat Buttons (*Tridax procumbens*), Cocklebur (*Xanthium* spp.), cocklebur (*Xanthium strumarium*), Common Beggartick (*Bidens alba*), common buckwheat, Common Burdock (*Arctium minus*), Common Chickweed (*Stellaria media*), Common Groundsel (*Senecio vulgaris*), Common Mallow, Common Milkweed (*Asclepias syriaca*), Common Mullein (*Verbascum thapsus*), common orache (*Atriplex patula*), Common Purslane (*Portulaca oleracea*), common radish, common ragweed (*Ambrosia artemisiifolia*), Common Sneezeweed (*Helenium amarum*), Common Sunflower (*Helianthus annuus*), Common Yarrow (*Achillea millefolium*), Compass Plant (*Silphium laciniatum*), conical catchfly, *Coreopsis* (*Coreopsis tinctoria*), corn chamomile, Corn Gromwell (*Lithospermum arvense*), Corn Speedwell (*Veronica arvensis*), corn spurry, Cowcockle (*Vaccaria pyramidata*), Cowpen Daisy (*Verbesina encelioides*), Crabgrass, large (*Digitaria sanguinalis*), Creeping Beggarweed (*Desmodium incanum*), creeping buttercup (*Ranunculus repens*), Creeping Cucumber (*Melothria pendula*), Creeping Indigo (*Indigofera spicata*), Creeping *Oxalis*, Creeping Speedwell, Creeping Woodsorrel (*Oxalis corniculata*), cress, *Croton*, Texas (*Croton texensis*), *Croton*, Tropic (*Croton glandulosus*), *Croton*, Woolly (*Croton capitatus*), Cup Plant (*Silphium perfoliatum*), Cupid's Shaving Brush (*Emilia sonchifolia*), Curly Dock (*Rumex crispus*), Curlycup Gumweed (*Grindelia squarrosa*), Cutleaf Eveningprimose (*Oenothera laciniata*), Cutleaf Groundcherry (*Physalis angulata*), Daisy Fleabane (*Erigeron annuus*), Dakota Verbena (*Verbena bipinnatifida*), Dandelion (*Taraxacum officinale*), Dayflower (*Commelina*), Deadnettle, Purple (*Lamium purpureum*), Devil's Claw (*Proboscidea louisianica*), Dichondra, Dogfennel (*Euphorbia capillifolium*), Elderberry (*Sambucus canadensis*), Englemann Daisy (*Englemannia pinnatifida*), false chamomile, False Daisy or Eclipta (*Eclipta prostrata*), False Nightshade (*Chamaesaracha coronopus*), field chickweed, Field Dodder (*Cuscuta campestris*), field pennycress, Filaree, redstem (*Erodium cicutarium*), Filaree, Texas or Storkbill (*Erodium texanum*), fixweed, Flixweed (*Descurainia sophia*), Florida Pellitory (*Parietaria floridana*), Fotail, bristly (*Setaria verticillata*), Foxtail, giant (*Setaria faberii*), Foxtail, green (*Setaria viridis*), Foxtail, yellow (*Setaria pumila*), Galinsoga (*Asteraceae* spp.), Galinsoga (*Galinsoga parviflora*), Garden Rocket (*Eruca vesicaria* ssp. *sativa*), Garden Spurge (*Chamaesyce hirta*), Germander (*Teucrium cubense*), Giant ragweed (*Ambrosia trifida*), Goldenrod (*Solidago* spp.), goosefoots (*Chenopodium* spp.), Gray Tidestrom (*Tidestromia lanuginosa*), Greenbriar (*Smilax* spp.), Greenthread (*Thelesperma filifolium*), Ground Spurge (*Euphorbia prostrata*), groundsel, Hairy Caltrop (*Kallstroemia hirsutissina*), Hairy Nightshade (*Solanum sarrachoides*), Hedge Parsley (*Torilis arvensis*), Hemp (*Cannabis sativa*), Hemp Dogbane (*Apocynum cannabinum*), Hemp Sesbania (*Sesbania exaltata*), Henbit (*Lamium amplexicaule*), Hogpotato (*Hoffmanseggia densiflora*), Honeysuckle (*Lonicera* spp.), Hophornbeam Copperleaf (*Acalypha ostryaefolia*), Horehound (*Marrubium vulgare*), Horse purslane (*Trianthema portulacastrum*), Horsenettle (*Solanum carolinense*), Horseweed (*Conyza canadensis*), Horseweed (marestail) (*Conyza canadensis*), Huisachedaisy (*Amblyolepis setigera*), Hyssop Spurge (*Chamaesyce hyssopifolia*), Illinois Bundleflower (*Desmanthus illinoensis*), Indian Blanket (*Gaillardia pulchella*), Indian Mallow (*Abutilon incana*), Japanese Hops (*Humulus japonicus*), Jerusalem Artichoke (*Helianthus tuberosus*), Jimsonweed (*Datura stramonium*), Khakiweed (*Alternanthera pungens*), knotweed (*polygonum* spp.), Knotweed, prostrate (*Polygonum aviculare*), Kochia (*Kochia scoparia*), Kudzu (noxious), Lambsquarters (*Chenopodium album*), Lanceleaf Sage (*Salvania reflexa*), Lantana (*Lantana camara*), Livid Amaranth (*Amaranthus blitum*), Lizardtail Gaura (*Gaura Parviflora*), London rocket, Long Fruited Primrose-Willow (*Ludwigia octovalvis*), Marijuana (noxious), Marsh Parsley (*Cyclospermum leptophylum*), marshelder, Match-Head (*Phyla nodiflora*), mayweed chamomile, Mexicanhat (*Ratibida columnaris*), Mexican-Poppy (*Argemone mexicana*), miners lettuce, Mock Bishop's Weed (*Ptilimnium capillaceum*), Morningglory ivyleaf, pitted (*Ipomoea hederacea*), Morningglory, Bigroot (*Ipomoea pandurata*), Morningglory, entireleaf (*Ipomoea hederacea* var. *integriuscula*), Morningglory, pitted (*Ipomoea lacunosa*), Morningglory, Sharppod (*Ipomoea trichocarpa*), Morningglory, Tall (*Ipomoea purpurea*), Mouseear Chickweed (*Cerastium vulgatum*), Mousetail (*Myosurus minimus*), Multiflora rose (noxious), Mustard, birdsrape (*Brassica rapa*), Mustard, black (*Brassica nigra*), Mustard, London Rocket (*Sisymbrium irio*), Mustard, Pinnatetansy (*Descurainia pinnate*), Mustard, Tansy (*Descurainia pinnata*), Mustard, Tumble (*Sisymbrium altissimum*), Mustard, Turnip Weed (*Rapistrum rugosum*), Mustard, Wild (*Brassica kaber*), narrowleaf lambsquarters, nightflowering catchfly, Nightshade, black (*Solanum nigrum*), Nightshade, eastern black (*Solanum ptycanthum*), Nodding Spurge (*Euphorbia nutans*), Nutsedge, yellow (*Cyperus esculentus*), Oat, wild (*Avena fatua*), Orange Globe Mallow (*Sphaeralcea occidentalis*), Oxeye Daisy (*Chrysanthemum leucanthemum*), Palmer Amaranth (*Amaranthus palmeri*), *Panicum*, fall (*Panicum dichotomiflorum*), Partridgepea (*Cassia chamaecrista*), Pennsylvania smartweed, Pennycress, Field (*Thlaspi arvense*), pigweed, Pigweed, smooth (*Amaranthus hybridus*), Pigweed, Tumble (*Amaranthus albus*), pineappleweed, plains *coreopsis*, Poison Hemlock (*Conium maculatum*), Pokeweed (*Phytolacca americana*), prickly lettuce, Prickly Pear (*Opuntia* spp.), Prickly Sida (*Sida spinosa*), Prostrate Knotweed (*Polygonum aviculare*), Prostrate pigweed (*Amaranthus blitoides*), Puncturevine (*Tribulus terrestris*), Purple Flower Groundcherry (*Physalis lobata*), Purple Horsemint (*Monarda citriodora*), Purple Loosestrife (noxious), Purslane Speedwell (*Veronica peregrina*), Pusley, FL (*Richardia scabra*), Rain Lily (*Cooperia drummondii*), Rattlesnake master (*Eryngium yuccifolium*), Red Hornedpoppy (*Glaucium corniculatum*), redmaids, redroot pigweed (*Amaranthus retroflexus*), Riddell Groundsel (*Senecio riddellii*), Rosinweed (*Silphium integrifolium*), Russian thistle, Ryegrass, Italian (*Lolium multiflorum*), Saltmarsh Fleabane (*Pluchea odorata*), Santa Maria or *Parthenium* Pancake Weed (*Parthenium hysterophorus*), Sawtooth aster (*Prionopsis ciliata*), Scarlet Gaura (*Gaura coccinea*), Scarlet Musk Flower (*Nyctaginia capitata*), scentless chamomile, Scrambledeggs (*Corydalis curvisiliqua*), sedges (*Carex* spp.), Shepherd's Purse (*Capsella bursa-pastoris*), Sicklepod (*Senna obtusifolia*), Signalgrass, broadleaf (*Brachiaria platyphylla*), SilverLeaf Cassia (*Cassia phyllodinea*), Silverleaf Nightshade (*Solanum elaeagnifolium*), Silversage (*Artemesia ludoviciana*), Silversheath Knotweed (*Polygonum argyrocoleon*), Skeletonweed (*Lygodesmia juncea*), Slender Aster (*Aster gracilis*), slender rush (*Juncus tenuis*), smallflower buttercup, Smallhead Sneezeweed (*Helenium microcephalum*), Smallseed Falseflax (*Camelina microcarpa*), smartweed, Smartweed, annual (*Polygonum pensylvanicum*), Smartweed, Pale (*Polygonum lapathifolium*), Smooth Groundcherry (*Physalis subglabrata*), Smooth Sumac (*Rhus glabra*), snow speedwell, Snow-on-the-mountain (*Euphorbia marginata*), Soft rush (*Juncus effuses*), Southern Sida (*Sida acuta*), Spiny Sowthistle (*Sonchus asper), Sprawling Horseweed (Calyptocarpus vialis), Spreading Dayflower (Commelina diffusa), Spurge, Leafy (Euphorbia esula), Spurge, Prostrate (Euphorbia humistrata), Spurge, Toothed (Euphorbia dentata), Spurred Anoda (Anoda cristata), sticky chickweed, stinking mayweed/dogfennel, Sweet-potato (Ipomea batatas), swinecress, Tahoka Daisy (Machaeranthera tanacetifolia), tansymustard, tarweed fiddleneck, Texas Blueweed (Helianthus ciliaris), Texas Bullnettle (Cnidoscolus texanus), Thistle, Blessed Milk (Silybum marianum), Thistle, Distaff (Carthamus lanatus), Thistle, Malta Star (Centaurea melitensis), Thistle, Musk (noxious), Thistle, Russian (Echinops exaltatus), Thistle, Scotch (noxious), Thistle, Tall (Cirsium altissimum), Thistle, Texas Purple (Cirsium texanum), Threadleaf Groundsel (Senecio longilobus), toad rush (Juncus bufonlus), Toothcup (Ammannia latifolia), Trumpetcreeper (Campsis radicans), tumble, Twinleaf Sennia (Senna roemeriana), Velvetleaf (Abutilon theophrasti), Venice Mallow (Hibiscus trionum), vetch (Vicia spp.), Virginia Copperleaf (Acalypha virginica), Virginia Creeper (Parthenocissus quinquefolia), Virginia Pepperweed (Lepidium virginicum), volunteer adzuki bean (Vigna angularis), volunteer lentils, volunteer peas, volunteer sunflower, Wandering Cudweed (Gnaphalium pensylvanicum), Waterhemlock (Cicuta maculata), Waterhemp (Amaranthus Rudis), Waterhemp (Amaranthus tuberculatus), Waterleaf (Nama hispidum), waterpod, Western Ragweed (Ambrosia psilostachya), Western Salsify (Tragopogon dubuis), White Foxglove Beardtongue (Penstemon digitalis), White Heath Aster (Aster pilosus), White Snakeroot (Eupatorium rugosum), Wild Buckwheat (Polygonum convolvulus), Wild Carrot (Daucus carota), wild chamomile, wild garlic, Wild Geranium (Geranium carolinanum), Wild Lettuce (Lactuca serriola), wild mustard (Sinapis arvensis), wild radish, Witchgrass (Panicum capillare), Woollyleaf Bursage (Ambrosia grayi), Woollywhite, Chalkhill (Hymenopappus tenuifolius), Woollywhite, Yellow (Hymenopappus flavescens), Wright Eryngo (Eryngium heterophyllum), Yellow Rocket (Barbarea vulgaris), Yellow Sweetclover (Melilotus indica).

Preferably, such weeds include Amaranthus spp., Ambrosia spp., Avena spp., Brachiaria spp., Carex spp., Digitaria spp., Echinops spp., Ipomoea spp., Juncus spp., Kochia spp., Lamium spp., Mollugo spp., Potentilla spp., Ranunculus spp., Sicyos spp., Solanum spp., Vicia spp., Xanthium spp.

More preferably, such weeds include Amaranth, Prostrate pigweed (Amaranthus blitoides), Amaranth, Powell (Amaranthus powellii), Waterhemp (Amaranthus rudis), Amaranth, spiny (Amaranthus spinosus), common ragweed (Ambrosia artemisiifolia), Giant ragweed (Ambrosia trifida), Oat, wild (Avena fatua), Signalgrass, broadleaf (Brachiaria platyphylla), sedges (Carex spp.), Crabgrass, large (Digitaria sanguinalis), Thistle, Russian (Echinops exaltatus), Morningglory ivyleaf, pitted (Ipomoea hederacea), Morningglory, pitted (Ipomoea lacunosa), toad rush (Juncus bufonlus), Canada Rush (Juncus Canadensis), Soft rush (Juncus effuses), slender rush (Juncus tenuis), Kochia (Kochia scoparia), Carpetweed (Mollugo verticillata), Amaranth, Palmer (Palmer Amaranth), cinquefoil (Potentilla spp.), creeping buttercup (Ranunculus repens), Burcucumber (Sicyos angulatus), vetch (Vicia spp.), cocklebur (Xanthium strumarium), Pigweed, smooth (Amaranthus hybridus), Deadnettle, Purple (Lamium purpureum), Nightshade, eastern black (Solanum ptycanthum).

The total amount of (A) and (B) is from 5% to 99% by weight of the composition.

The crystalline modification I of mesotrione may be present in the synergistic herbicidal composition of an embodiment of the invention in any suitable amount, and is generally present in an amount of from about 1% to about 90% by weight of the composition, preferably from about 1% to 80% by weight, more preferably from about 1% to about 70%, still more preferably from about 10% to about 60% by weight of the composition.

The crystalline modification I of rimsulfuron may be present in the synergistic herbicidal composition in any suitable amount, and is generally present in an amount of from about 0.1% to about 90% by weight of the composition, preferably from about 1% to about 80% by weight, more preferably from about 1% to about 70% by weight of the composition, more preferably from about 1% to about 60%, still more preferably from about 1% to about 30%.

(A) and (B) may be employed in the composition, method or use of the present invention in any suitable weight ratio. The weight ratio of the crystalline modification I of mesotrione and the crystalline modification I of rimsulfuron in the composition may be in the range of from about 150:1 to about 1:50, preferably from about 100:1 to about 1:25, more preferably from about 50:1 to about 1:10, more preferably from about 40:1 to about 1:3, more preferably still from about 15:1 to about 1:3, and most preferably about 10:1.

In general, the application rate of the active ingredients depends on such factors as the type of weed, type of crop plant, soil type, season, climate, soil ecology and various other factors. The application rate of the composition for a given set of conditions can readily be determined by routine trials.

In general the composition or the method of the present invention can be applied at an application rate of from about 0.005 kilograms/hectare (kg/ha) to about 5.0 kg/ha of the total amount of active ingredient (A) and (B) being applied. Preferably, the application rate is from about 0.01 kg/ha to about 3.0 kg/ha of the active ingredients.

Preferably, the application rate of the active ingredients is from 1 to 1000 g/ha of (A) the crystalline modification I of mesotrione and from 0.1 to 250 g/ha of (B) the crystalline modification I of rimsulfuron. More preferably, the application rate of the active ingredients is from 1 to 250 g/ha of (A) the crystalline modification I of mesotrione and from 1 to 100 g/ha of (B) the crystalline modification I of rimsulfuron. Even more preferably, the application rate of the active ingredients is from 1 to 200 g/ha of (A) the crystalline modification I of mesotrione and from 1 to 75 g/ha of (B) the crystalline modification I of rimsulfuron.

As noted above, in an embodiment of the invention, (A) the crystalline modification I of mesotrione and (B) the crystalline modification I of rimsulfuron may be applied either separately or combined as part of a two-part herbicidal system, such as the composition of an embodiment of the invention. The composition is applied pre-planting, pre-emergence and/or post-emergence.

The compositions of an embodiment of this invention can be formulated in conventional manner, for example by mixing (A) the crystalline modification I of mesotrione and (B) the crystalline modification I of rimsulfuron with appropriate auxiliaries. Suitable auxiliaries will depend upon such factors as the type of formulation and will be known to the person skilled in the art.

In particular, the composition may further comprise one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents. Such auxiliaries are known in the art and are commercially available. Their use in the formulation of the compositions of the present invention will be apparent to the person skilled in the art.

Suitable formulations for applying a combination of (A) and (B) include water-soluble concentrates (SL), emulsifiable concentrates (EC), emulsions, oil in water (EW), microemulsions (ME), suspension concentrates (SC), oil-based suspension concentrates (OD), flowable suspensions (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). Preferred formulations are suspension concentrates (SC), water-dispersible granules (WG) and water-soluble granules (SG).

The composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks, and mixtures thereof.

The composition may optionally include one or more surfactants which are preferably non-ionic, cationic and/or anionic in nature and surfactant mixtures which have good emulsifying, dispersing and wetting properties, depending upon the active compound/compounds being formulated. Suitable surfactants are known in the art and are commercially available.

Suitable anionic surfactants can be both so-called water-soluble soaps and water-soluble synthetic surface-active compounds. Soaps which may be used include the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The surfactant may comprise an emulsifier, dispersant or wetting agent of ionic or nonionic type. Examples of such agents include salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, and phosphoric esters of polyethoxylated phenols or alcohols.

The presence of at least one surfactant is generally required when the active compound and/or the inert carrier and/or auxiliary/adjuvant are insoluble in water and the vehicle for the final application of the composition is water.

The composition may optionally further comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foaming agents for use in the compositions include all substances which can normally be used for this purpose in agrochemical compositions. Suitable anti-foaming agents are known in the art and are available commercially. Particularly preferred antifoam agents are mixtures of polydimethylsiloxanes and perfluroalkylphosphonic acids, such as the silicone anti-foaming agents available from GE or Compton.

Suitable solvents for use in the compositions may be selected from all customary organic solvents which thoroughly dissolve the active compounds employed. Again, suitable organic solvents for (A) and (B) are known in the art. The following may be mentioned as being preferred: N-methyl pyrrolidone, N-octyl pyrrolidone, cyclohexyl-1-pyrrolidone; and a mixture of paraffinic, isoparaffinic, cycloparaffinic and aromatic hydrocarbons (available commercially as SOLVESSO™200). Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

The compositions may comprise an antioxidant. Suitable antioxidants are all substances which can normally be used for this purpose in agrochemical compositions, as is known in the art. Preference is given to butylated hydroxytoluene.

Suitable thickening agents for use in the compositions include all substances which can normally be used for this purpose in agrochemical compositions. Examples include xanthan gum, PVOH, cellulose and its derivatives, clay hydrated silicates, magnesium aluminum silicates or a mixture thereof. Again, such thickening agents are known in the art and available commercially.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to the invention may also comprise water.

The formulated composition may for example be applied in spray form, for example employing appropriate dilutions using a diluent, such as water.

In the method and use of an embodiment of the invention, the combination of the active ingredients can be applied to the locus where control is desired, such as to the leaves of plants and/or the surrounding soil, by a convenient method.

In the event, (A) and (B) are applied simultaneously in an embodiment of the invention, they may be applied as a composition containing (A) and (B), in which case (A) and (B) can be obtained from a separate formulation source and mixed together (known as a tank-mix, ready-to-apply, spray broth, or slurry), optionally with other pesticides, or (A) and (B) can be obtained as a single formulation mixture source (known as a pre-mix, concentrate, formulated compound (or product)), and optionally mixed together with other pesticides.

In a preferred embodiment, the method and use of the invention employ a composition according to an embodiment of the invention.

The compositions according to an embodiment of the invention are distinguished by the fact that they are especially well tolerated by crop plants being treated and are environmentally friendly.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

Embodiments of the present invention will now be described, for illustrative purposes only, by way of the following examples.

EXAMPLES

Example 1

Preparation of the Crystalline Modification I Mesotrione

The crystalline modification I of mesotrione was prepared according to the method as mentioned in WO2006021743.

Mesotrione enolate suspension was filtered to remove any excess solid enolate. 50 mL of the filtered solution was placed in a reaction flask and heated to 40° C. The pH of the solution was adjusted to 2.8 by adding 10% HCl over 20 minutes. The crystals were allowed to stir for 20 minutes before isolation by filtration. The crystals were then washed with water and sucked dry on the filter.

Example 2

Preparation of the Crystalline Modification II Mesotrione

The crystalline modification II of mesotrione was prepared according to the method as mentioned in WO2006021743.

Mesotrione crystals were stirred with water in a reaction flask. The pH was increased to 12 by adding NaOH. 1.5 mL of 10% HCl was added over 15 minutes to reduce the pH of the solution to pH 4. Crystals were obtained.

Example 3

Preparation of Amorphous Rimsulfuron in Accordance with the Disclosure of EP0341011 A1

To a stirred suspension of 0.60 g (0.0024 mol) of 3-ethylsulfonyl-2-pyridinesulfonamide and 0.90 g (0.0034 mol) of phenyl (4,6-dimethoxypyrimidin-2-yl)carbamate in 5 mL acetonitrile, 0.52 g (0.0034 mol) of 1,8-diazabicyclo[5.4.0]undec-7-ene (DBU) was added and stirred for 15 minutes. The solution was diluted with water and acidified with hydrochloric acid. The resulting solid precipitate was collected and washed with water and ether to give 0.70 g (70%) of the title compound: melting point of 160° C.-162° C.

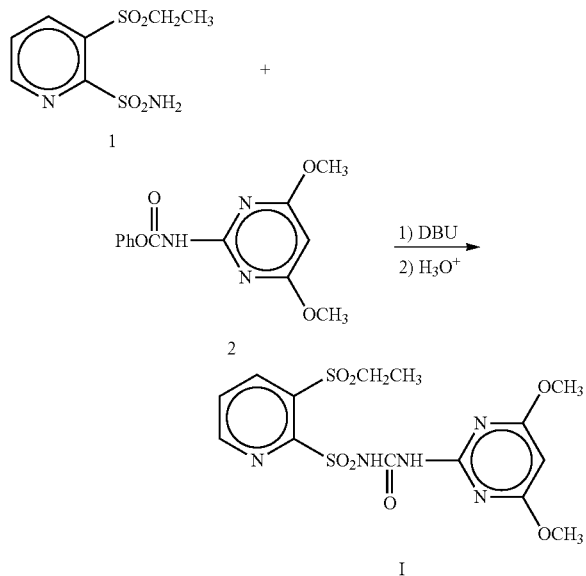

Figure 3:
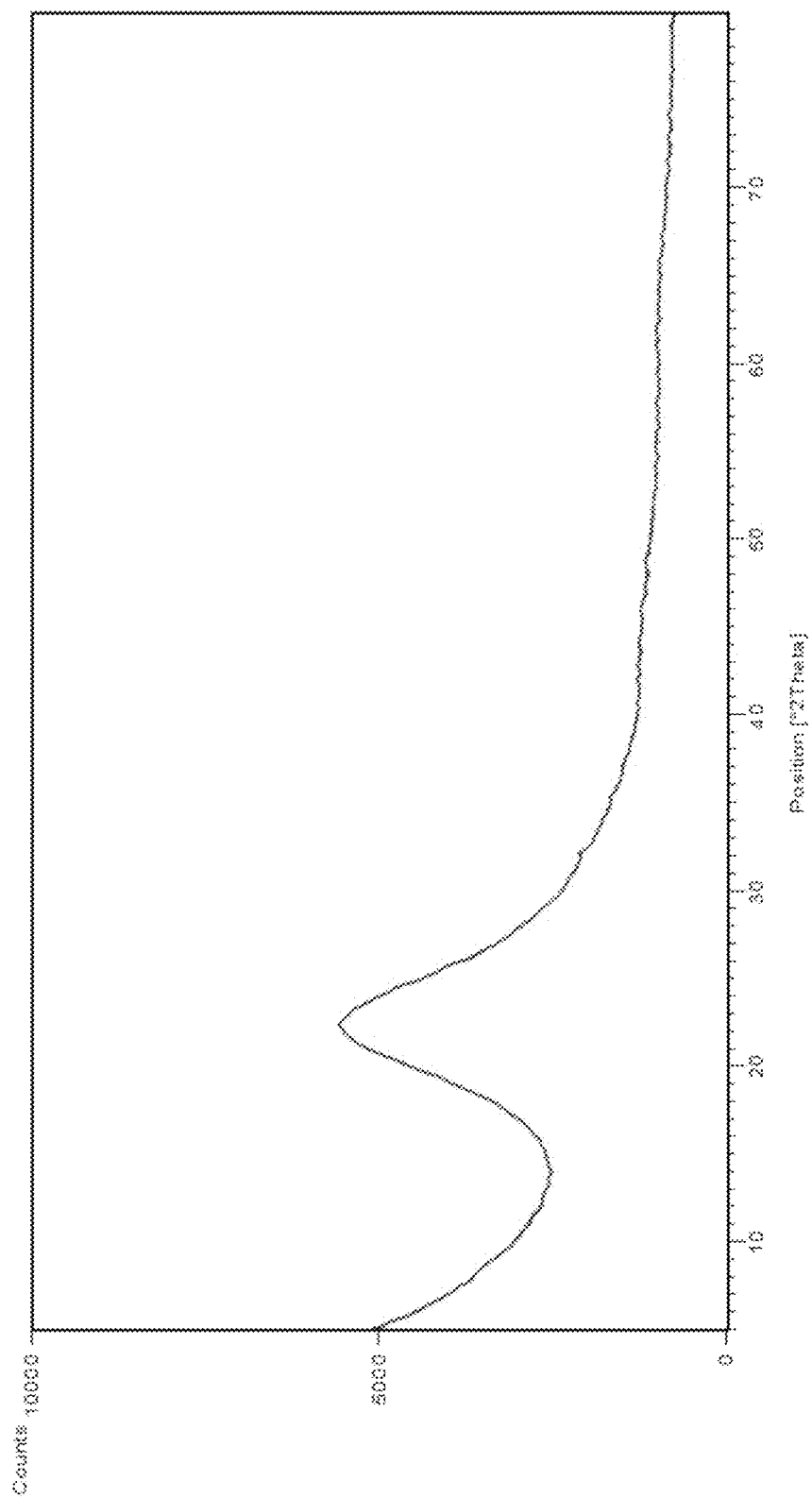
FIG. 3 is an X-ray powder diffractogram of amorphous rimsulfuron.

As shown in FIG. 3, the X-ray powder diffraction pattern of the resulting rimsulfuron product has no significant signals, which indicates the rimsulfuron product prepared in accordance with the disclosure of EP0341011 A1 is amorphous.

Example 4

Preparation of the Crystalline Modification I of Rimsulfuron (Crystallization from Methanol)

10 mL methanol was charged into the reactor to dissolve crude rimsulfuron prepared in example 3 under stirring. This process lasted for 2 hours under room temperature, and white solid precipitate appeared. The mixture was then cooled down to 0° C.-5° C. and maintained for 1 hour to allow complete crystallization. After that, the mixture was centrifuged. The filter cake was washed with methanol. The resulting solid was dried under high vacuum to give crystals of pure rimsulfuron technical (Purity: 98%).

The crystals were characterized as being of the crystalline modification I of rimsulfuron using both IR spectrometry and X-ray powder diffraction.

The IR spectrum of the crystalline modification I of rimsulfuron is set out in FIG. 1. The IR spectrum exhibits characteristic peaks at 3257.17 $cm^{-1}$ and 2943.91 $cm^{-1}$.

Figure 2:
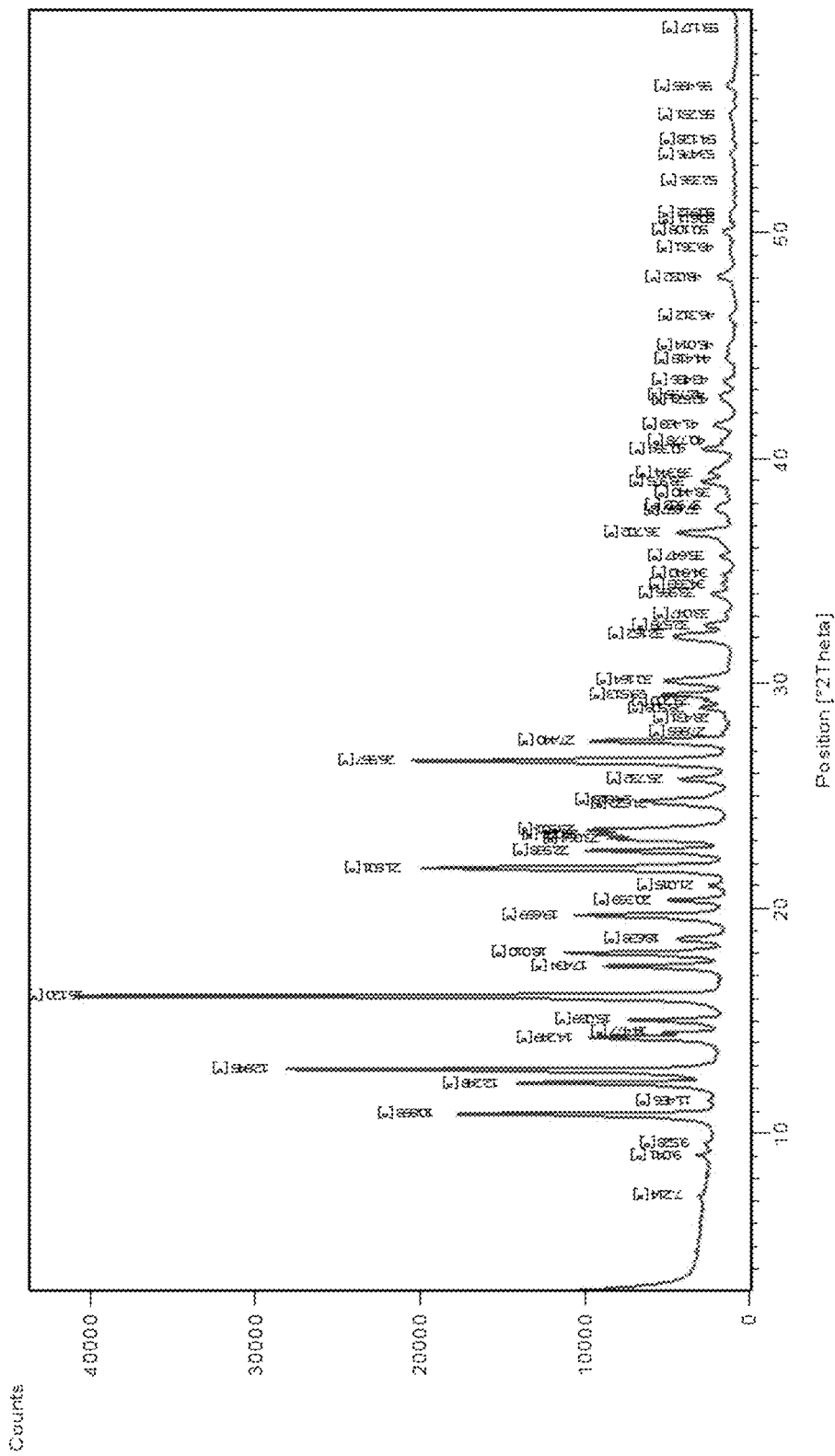
FIG. 2 is an X-ray powder diffractogram (XRD) of crystalline modification I of rimsulfuron, according to an embodiment of the invention.

The crystalline modification I of rimsulfuron has the X-ray powder diffractogram shown in FIG. 2 with the reflexes listed in Table 1 below.

TABLE 1

| Crystal Form A | |
|---|---|
| 2 θ (°) | d (Å) |
| 10.868 ± 0.2 | 8.14 ± 0.05 |
| 12.248 ± 0.2 | 7.23 ± 0.05 |
| 12.845 ± 0.2 | 6.89 ± 0.05 |
| 14.249 ± 0.2 | 6.22 ± 0.05 |
| 15.039 ± 0.2 | 6.12 ± 0.05 |
| 16.120 ± 0.2 | 5.50 ± 0.05 |
| 17.434 ± 0.2 | 5.09 ± 0.05 |
| 18.010 ± 0.2 | 4.93 ± 0.05 |
| 19.699 ± 0.2 | 4.51 ± 0.05 |
| 21.801 ± 0.2 | 4.08 ± 0.05 |
| 22.568 ± 0.2 | 3.94 ± 0.05 |
| 26.567 ± 0.2 | 3.56 ± 0.05 |

Example 5

Preparation of the Crystalline Modification I of Rimsulfuron (Crystallization from Ethanol)

10 mL ethanol was charged into the reactor to dissolve crude rimsulfuron prepared in example 1 under stirring. This process lasted for 2 hours under room temperature, and white solid precipitate appeared. The mixture was then cooled down to 0° C.-5° C. and maintained for 1 hour to allow complete crystallization. After that, the mixture was centrifuged. The filter cake was washed with some ethanol. The resulting solid was dried under high vacuum to give crystals of pure rimsulfuron technical (Purity: 98%).

The crystals were characterized as being the crystalline modification I of rimsulfuron using IR spectrometry and X-ray powder diffraction as described in Example 4.

Formulation Examples

Water-dispersible granule (WG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) under compressed air, then wetting, extruding and drying to obtain water-dispersible granule.

For example,

| | |
|---|---|
| The crystalline modification I of mesotrione | 50% |
| The crystalline modification I of rimsulfuron | 12% |
| SUPRALATE ® (sodium lauryl sulfate, Witco Inc., Greenwich) | 0.5% |
| REAX ®88B (sodium lignosulfonate, Westvaco Corp) | 5% |
| Potassium carbonate | Balance to 100% |

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,

| | |
|---|---|
| The crystalline modification I of mesotrione | 40% |
| The crystalline modification I of rimsulfuron | 4% |
| Propylene glycol | 10% |
| Tristyrylphenol ethoxylates | 5% |
| Sodium lignosulfonate | 1% |
| Carboxymethylcellulose | 1% |
| Silicone oil (in the form of a 75% emulsion in water) | 1% |
| Xanthan gum | 0.1% |
| NIPACIDE BIT 20 | 0.1% |
| Water | Balance to 1 L |

Water-soluble granules (SG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), 2% Sodium hydrogen carbonate (NaHCO$_3$), Potassium sulfate (balance to 100%)) under compressed air, then wetting, extruding and drying to obtain water-soluble granules.

For example,

| | |
|---|---|
| The crystalline modification I of mesotrione | 30% |
| The crystalline modification I of rimsulfuron | 2% |
| SUPRALATE ® (sodium lauryl sulfate, Witco Inc., Greenwich) | 0.5% |
| REAX ® 88B (sodium lignosulfonate, Westvaco Corp) | 5% |
| Sodium hydrogen carbonate (NaHCO$_3$) | 2% |
| Potassium sulfate | Balance to 100% |

Formulations were prepared according to the method above (Table A):

TABLE A

| Formulation No. | type | Mesotrione (%) I | Mesotrione (%) II | Rimsulfuron (%) Amorphous | Rimsulfuron (%) I |
|---|---|---|---|---|---|
| 1 | SC | 40 | / | / | / |
| 2 | SC | / | 40 | / | / |
| 3 | WG | / | / | 10 | / |
| 4 | WG | / | / | / | 10 |
| 5 | SC | 40 | / | 4 | / |
| 6 | SC | / | 40 | 4 | / |
| 7 | SC | 40 | / | / | 4 |
| 8 | SC | / | 40 | / | 4 |
| 9 | SC | 40 | / | / | 4 |
| 10 | WG | 50 | / | / | 12 |
| 11 | SC | 40 | / | / | 8 |
| 12 | SG | 30 | / | / | 2 |
| 13 | WG | 60 | / | / | 6 |
| 14 | SC | 20 | / | / | 20 |
| 15 | SG | 10 | / | / | 30 |
| 16 | SC | 40 | / | / | 1 |

Biological Examples 1

A synergistic effect exists with a combination of two active compounds when the activity of a composition comprising both active compounds is greater than the sum of the activities of the two active compounds applied individually. The expected activity for a given combination of two active compounds can be calculated by the so called "Colby equation" (see S. R. Colby, "Calculating Synergistic and Antagonistic Responses of Herbicide Combinations", Weeds 1967, 15, 20-22):

whereby:

A=the efficiency % of compound A when active compound A is employed at an application rate of m g/ha;

B=the efficiency % of compound B when active compound B is employed at an application rate of n g/ha;

E=the efficiency % of estimated activity when compounds A and B are employed together at an application rate of m g/ha and n g/ha;

then:

$$E=A+B-(A \times B/100).$$

If the actual activity observed for the combination of compounds A and B is greater than that calculated, then the activity of the combination is superadditive. In other words, synergism is present.

Corn, potato and tomato plants were sown side by side in the field. Different types of weeds and their relative density were recorded and are listed in Table 2 below. Formulations of Examples 1 to 8 above were applied 50 days after planting. After application, the beds were maintained for about two weeks. Two weeks after application, the beds were examined to determine the efficiency of the treatment. The results are set forth below in Table 3 below.

TABLE 2

| Type of weed | |
|---|---|
| Type of weed | Relative density (%) |
| *Amaranthus* spp. | 10 |
| *Ambrosia* spp. | 5 |
| *Avena* spp. | 15 |
| *Brachiaria* spp. | 20 |
| *Digitaria* spp. | 10 |
| *Kochia* spp. | 5 |
| *Lamium* spp. | 10 |
| *Mollugo* spp. | 5 |
| *Xanthium* spp. | 20 |

TABLE 3

| Formulation Examples | Mesotrione (g/ha) | Rimsulfuron (g/ha) | Efficiency (%) Type of weed | | | | | | | | |
|---|---|---|---|---|---|---|---|---|---|---|---|
| | | | *Amaranthus* spp. | *Ambrosia* spp. | *Avena* spp. | *Brachiaria* spp. | *Digitaria* spp. | *Kochia* spp. | *Lamium* spp. | *Mollugo* spp. | *Xanthium* spp. |
| Untreated | 0 | 0 | 0 | 0 | 0 | 0 | 0 | 0 | 0 | 0 | 0 |
| Example 1 | 100 | 0 | 25 | 25 | 30 | 35 | 35 | 30 | 40 | 30 | 35 |
| Example 2 | 100 | 0 | 30 | 30 | 35 | 35 | 40 | 40 | 45 | 35 | 35 |
| Example 3 | 0 | 10 | 25 | 25 | 35 | 35 | 45 | 30 | 30 | 50 | 45 |
| Example 4 | 0 | 10 | 25 | 20 | 35 | 30 | 45 | 35 | 35 | 50 | 40 |
| Example 5 | 100 | 10 | 35 | 35 | 40 | 45 | 35 | 35 | 45 | 50 | 40 |
| Example 6 | 100 | 10 | 35 | 35 | 30 | 40 | 30 | 35 | 35 | 40 | 35 |
| Example 7 | 100 | 10 | 95 | 95 | 90 | 100 | 100 | 90 | 100 | 95 | 100 |
| Example 8 | 100 | 10 | 45 | 45 | 40 | 50 | 55 | 55 | 50 | 50 | 50 |

Biological Examples 2

Soybean, wheat and cotton plants were sown side by side in the field. Different types of weeds and their relative density were recorded and are listed in Table 4 below. Formulations of Examples 9 to 16 above were applied 50 days after planting. After application, the beds were maintained for about 2 weeks. Two weeks after application, the beds were examined to determine the efficiency of the treatment. The results are set forth below in Table 5 below.

TABLE 4

| Type of weed | Relative density (%) |
|---|---|
| *Carex* spp. | 5 |
| *Echinops* spp. | 10 |
| *Ipomoea* spp. | 15 |
| *Juncus* spp. | 15 |
| *Potentilla* spp. | 5 |
| *Ranunculus* spp. | 10 |
| *Sicyos* spp. | 5 |
| *Solanum* spp. | 20 |
| *Vicia* spp. | 15 | urea (rimsulfuron), wherein the crystalline modification I of rimsulfuron is crystallized using methanol and/or ethanol, and the crystalline modification I of rimsulfuron exhibits each of following reflexes as $2\theta$ values in an X-ray powder diffractogram recorded using Cu-K$\alpha$ radiation at 25° C.:

$$2\theta=10.868\pm0.2 \quad (1)$$

$$2\theta=12.248\pm0.2 \quad (2)$$

$$2\theta=12.845\pm0.2 \quad (3)$$

$$2\theta=14.249\pm0.2 \quad (4)$$

$$2\theta=15.039\pm0.2 \quad (5)$$

$$2\theta=16.120\pm0.2 \quad (6)$$

$$2\theta=17.434\pm0.2 \quad (7)$$

$$2\theta=18.010\pm0.2 \quad (8)$$

$$2\theta=19.699\pm0.2 \quad (9)$$

$$2\theta=21.801\pm0.2 \quad (10)$$

TABLE 5

| Formulation Examples | Mesotrione (g/ha) | Rimsulfuron (g/ha) | Efficiency (%) Type of weed | | | | | | | | |
|---|---|---|---|---|---|---|---|---|---|---|---|
| | | | *Carex* spp. | *Echinops* spp. | *Ipomoea* spp. | *Juncus* spp. | *Potentilla* spp. | *Ranunculus* spp. | *Sicyos* spp. | *Solanum* spp. | *Vicia* spp. |
| Untreated | 0 | 0 | 0 | 0 | 0 | 0 | 0 | 0 | 0 | 0 | 0 |
| Example 9 | 100 | 10 | 100 | 95 | 95 | 95 | 100 | 90 | 95 | 100 | 95 |
| Example 10 | 125 | 30 | 95 | 90 | 95 | 90 | 90 | 95 | 90 | 100 | 100 |
| Example 11 | 100 | 20 | 100 | 95 | 95 | 90 | 90 | 90 | 95 | 100 | 100 |
| Example 12 | 75 | 5 | 95 | 90 | 95 | 90 | 95 | 95 | 90 | 95 | 95 |
| Example 13 | 150 | 15 | 100 | 95 | 95 | 90 | 95 | 95 | 100 | 95 | 100 |
| Example 14 | 50 | 50 | 90 | 90 | 90 | 95 | 90 | 95 | 95 | 95 | 95 |
| Example 15 | 25 | 75 | 90 | 90 | 90 | 90 | 90 | 95 | 95 | 90 | 90 |
| Example 16 | 100 | 2.5 | 95 | 90 | 90 | 90 | 95 | 95 | 95 | 90 | 90 |

$$2\theta=22.568\pm0.2 \quad (11)$$

$$2\theta=26.567\pm0.2 \quad (12).$$

The invention claimed is:

1. A composition comprising a herbicidally effective amount of
    (A) the crystalline modification I of 2-(4-mesyl-2-nitrobenzoyl)cyclohexane-1,3-dione (mesotrione); and
    (B) the crystalline modification I of 1-(4,6-dimethoxypyrimidin-2-yl)-3-(3-ethylsulfonyl-2-pyridylsulfonyl)

2. The composition according to claim 1, wherein the weight ratio of (A) to (B) is in the range of from about 150:1 to about 1:50.

3. The composition according to claim 2, wherein the weight ratio of (A) to (B) is in the range of from about 40:1 to about 1:3.

4. The composition according to claim 3, wherein the weight ratio of (A) to (B) is about 10:1.

5. The composition according to claim 1, wherein the total amount of (A) and (B) is from 5% to 99% by weight of the composition.

6. The composition according to claim 5, wherein the composition comprises, by weight, from about 1% to about 90% of (A) and from about 0.1% to about 90% of (B).

7. The composition according to claim 5, wherein the composition comprises, by weight, from about 1% to about 70% of (A) and from about 1% to about 60% of (B).

8. The composition according to claim 1, further comprising one or more auxiliaries selected from the group consisting of extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents.

9. The composition according to claim 1, formulated as a water-soluble concentrate (SL), an emulsifiable concentrate (EC), an emulsion, oil in water (EW), a micro-emulsion (ME), a suspension concentrate (SC), an oil-based suspension concentrate (OD), a flowable suspension (FS), a water-dispersible granule (WG), a water-soluble granule (SG), a wettable powder (WP), a water soluble powder (SP), a granule (GR), an encapsulated granule (CG), a fine granule (FG), a macrogranule (GG), an aqueous suspo-emulsion (SE), a capsule suspension (CS) or a microgranule (MG).

10. A method of controlling undesirable plant growth comprising applying to the plant or to the locus thereof a herbicidally effective amount of the herbicidal composition of claim 1.

11. The method according to claim 10, wherein the plant growth is being controlled in a crop comprising cereals, fruits, vegetables, fibre and leguminous plants.

12. The method according to claim 10, wherein the plant growth being controlled is of one or more of broadleaf weeds, grasses and sledges.

13. The method according to claim 12, wherein the plant growth being controlled is one or more of *Amaranthus* spp., *Ambrosia* spp., *Avena* spp., *Brachiaria* spp., *Carex* spp., *Digitaria* spp., *Echinops* spp., *Ipomoea* spp., *Juncus* spp., *Kochia* spp., *Lamium* spp., *Mollugo* spp., *Potentilla* spp., *Ranunculus* spp., *Sicyos* spp., *Solanum* spp., *Vicia* spp., and *Xanthium* spp.

14. The method according to claim 10, wherein the composition is applied at an application rate of about 0.005 kilograms/hectare (kg/ha) to about 5.0 kg/ha of the total amount of active ingredient (A) and (B) being applied.

15. The method according to claim 14, wherein the composition is applied at an application rate of from about 0.01 kg/ha to about 3.0 kg/ha of the total amount of active ingredient (A) and (B) being applied.

16. The method according to claim 15, wherein the composition is applied at an application rate of from 1 to 1000 g/ha of (A) and from 0.1 to 250 g/ha of (B).

17. The method according to claim 16, wherein the composition is applied at an application rate of from 1 to 200 g/ha of (A) and 1 to 75 g/ha of (B).

18. The method according to claim 10, wherein the composition is applied pre-planting, pre-emergence and/or post-emergence.

19. A method of controlling undesirable plant growth at a locus comprising applying to the locus herbicidally effective amounts of (A) the crystalline modification I of 2-(4-mesyl-2-nitrobenzoyl)cyclohexane-1,3-dione (mesotrione) and (B) the crystalline modification I of 1-(4,6-dimethoxypyrimidin-2-yl)-3-(3-ethylsulfonyl-2-pyridylsulfonyl)urea (rimsulfuron), wherein the crystalline modification I of rimsulfuron is crystallized using methanol and/or ethanol, and the crystalline modification I of rimsulfuron exhibits each of following reflexes as 2θ values in an X-ray powder diffractogram recorded using Cu-Kα radiation at 25° C.:

$$2\theta = 10.868 \pm 0.2 \quad (1)$$
$$2\theta = 12.248 \pm 0.2 \quad (2)$$
$$2\theta = 12.845 \pm 0.2 \quad (3)$$
$$2\theta = 14.249 \pm 0.2 \quad (4)$$
$$2\theta = 15.039 \pm 0.2 \quad (5)$$
$$2\theta = 16.120 \pm 0.2 \quad (6)$$
$$2\theta = 17.434 \pm 0.2 \quad (7)$$
$$2\theta = 18.010 \pm 0.2 \quad (8)$$
$$2\theta = 19.699 \pm 0.2 \quad (9)$$
$$2\theta = 21.801 \pm 0.2 \quad (10)$$
$$2\theta = 22.568 \pm 0.2 \quad (11)$$
$$2\theta = 26.567 \pm 0.2 \quad (12).$$

20. The method according to claim 19, wherein the plant growth is being controlled in a crop comprising cereals, fruits, vegetables, fibre and leguminous plants.

21. The method according to claim 19, wherein (A) and (B) are applied to the locus at the same time.

22. The method according to claim 19, wherein (A) and (B) are applied to the locus consecutively.

23. The method according to claim 19, wherein the plant growth being controlled is of one or more of broadleaf weeds, grasses and sledges.

24. The method according to claim 23, wherein the plant growth being controlled is one or more of *Amaranthus* spp., *Ambrosia* spp., *Avena* spp., *Brachiaria* spp., *Carex* spp., *Digitaria* spp., *Echinops* spp., *Ipomoea* spp., *Juncus* spp., *Kochia* spp., *Lamium* spp., *Mollugo* spp., *Potentilla* spp., *Ranunculus* spp., *Sicyos* spp., *Solanum* spp., *Vicia* spp., and *Xanthium* spp.

25. The method according to claim 19, wherein the weight ratio of (A) to (B) applied is in the range of from about 150:1 to about 1:50.

26. The method according to claim 25, wherein the weight ratio of (A) to (B) applied is in the range of from about 40:1 to about 1:3.

27. The method according to claim 26, wherein the weight ratio of (A) to (B) applied is about 10:1.

28. The method according to claim 19, wherein (A) and (B) are applied at an application rate of about 0.005 kilograms/hectare (kg/ha) to about 5.0 kg/ha of the total amount of active ingredient (A) and (B) being applied.

29. The method according to claim 28, wherein (A) and (B) are applied at an application rate of from about 0.01 kg/ha to about 3.0 kg/ha of the total amount of active ingredient (A) and (B) being applied.

30. The method according to claim 29, wherein (A) and (B) are applied at an application rate of from 1 to 1000 g/ha of (A) and from 0.1 to 250 g/ha of (B).

31. The method according to claim 30, wherein (A) and (B) are applied at an application rate of from 1 to 200 g/ha of (A) and 1 to 75 g/ha of (B).

32. The method according to claim 19, wherein (A) and (B) are applied pre-planting, pre-emergence and/or post-emergence.

\* \* \* \* \*